(12) United States Patent
Lean et al.

(10) Patent No.: US 7,156,970 B2
(45) Date of Patent: Jan. 2, 2007

(54) DISTRIBUTED MULTI-SEGMENTED RECONFIGURABLE TRAVELING WAVE GRIDS FOR SEPARATION OF PROTEINS IN GEL ELECTROPHORESIS

(75) Inventors: Meng H. Lean, Santa Clara, CA (US); Huangpin Ben Hsieh, Mountain View, CA (US); John S. Fitch, Los Altos, CA (US); Armin R. Völkel, Mountain View, CA (US); Bryan Preas, Palo Alto, CA (US); Scott Elrod, La Honda, CA (US); Richard H. Bruce, Los Altos, CA (US); Eric Peeters, Fremont, CA (US); Frank Torres, San Jose, CA (US); Michael Chabinyc, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 749 days.

(21) Appl. No.: 10/459,799

(22) Filed: Jun. 12, 2003

(65) Prior Publication Data

US 2004/0251135 A1     Dec. 16, 2004

(51) Int. Cl.
*G01N 27/447* (2006.01)
*G01N 27/453* (2006.01)

(52) U.S. Cl. ...................... 204/547; 204/643
(58) Field of Classification Search ................ 204/547, 204/643
See application file for complete search history.

(56) References Cited

U.S. PATENT DOCUMENTS

| | | | |
|---|---|---|---|
| 4,473,452 A | 9/1984 | Cantor et al. | |
| 4,647,179 A | 3/1987 | Schmidlin | |
| 4,737,251 A | 4/1988 | Carle et al. | |
| 5,208,458 A | 5/1993 | Busch et al. | |
| 5,534,121 A | 7/1996 | Merrick et al. | |
| 5,653,859 A | 8/1997 | Parton et al. | |
| 5,837,116 A | 11/1998 | Harrington et al. | |
| 5,993,632 A * | 11/1999 | Becker et al. | 204/547 |
| 6,272,296 B1 | 8/2001 | Gartstein | |
| 6,358,752 B1 | 3/2002 | Durst et al. | |
| 6,398,933 B1 | 6/2002 | Scott | |
| 6,499,831 B1 | 12/2002 | Schmidlin | |

(Continued)

FOREIGN PATENT DOCUMENTS

WO     WO 00/73780     12/2000

(Continued)

OTHER PUBLICATIONS

Morishima et al. ("Novel separation method in a Chip using Capillary Electrophoresis in Combination with Dielectrophoresis," Micro Total Analysis Systems 2000. 269-272).*

(Continued)

*Primary Examiner*—Alex Noguerola
(74) *Attorney, Agent, or Firm*—Fay, Sharpe, Fagan, Minnich & McKee, LLP

(57) ABSTRACT

Various traveling wave grids and electrophoretic systems, and electrode assemblies using such grids, are disclosed. A configuration in which a voltage potential is used to load a biomolecule sample against a grid is disclosed. A unique strategy of using multiple, reconfigurable grids in such systems is also described. The strategy involves initially conducting a broad protein separation and then selectively tailoring one or more grids, and conducting one or more secondary processing operations. Related strategies and specific methods are additionally disclosed for separating samples of biomolecules and components thereof using the noted systems, assemblies, and grids.

20 Claims, 11 Drawing Sheets

U.S. PATENT DOCUMENTS

| | | | |
|---|---|---|---|
| 6,761,811 B1 * | 7/2004 | Mariella, Jr. | 204/547 |
| 2001/0023825 A1 | 9/2001 | Frumin et al. | |
| 2002/0144895 A1 | 10/2002 | Stern et al. | |

FOREIGN PATENT DOCUMENTS

| | | |
|---|---|---|
| WO | WO 02/27909 | 4/2002 |
| WO | WO 02/31506 | 4/2002 |

OTHER PUBLICATIONS

Bakewell et al. ("Characterisation of the dielectrophoretic movement of DNA in micro-fabricated structures," Inst. Phys. Conf. Ser. No. 163, Paper presented at the 10th Int. Conf., Cambridge, Mar. 28-31, 1998).*

Ajdari et al. ("Free-flow electrophoresis with trapping by a transverse inhomogeneous field," Proc. Natl. Acad. Sci. USA, vol. 88, pp. 4468-4471, May 1991).*

Masuda et al., "Separation of Small Particles Suspended in Liquid by Nonuniform Traveling Field," IEEE Transactions on Industry Applications, IEEE Inc., New York, US, vol. IA 23, No. 3, May 1, 1987, pp. 474-480.

Scott Rudge et al., Electroseparations (Electrophoresis), *Encyclopedia of Chemical Technology*, 4th Edition, vol. 9, pp. 356-376.

O'Hara et al., *Ratcheting Electrophoresis Microchip (REM) for Programmable Transport and Separation of Macromolecules*, MEMS, Nov. 11-16, 2001, pp. 619-628, vol. 3, ASME, USA.

Dunphyet al., *Rapid Separation and Manipulation of DNA by a Ratcheting Electrophoresis Microchip (REM)*, Nov. 17-22, 2002, pp. 419-423, ASME, USA.

Proteome Systems, Products, Website, *ElectrophoretIQ³*, 2002 at http://www.proteomesystems.com/product/product.asp-?ProductID=43 and http://www.proteomesystems.com/product/profile.asp?DocumentID=662.

ISC Buyers' Guide, Website, *Electrophoresis, 2D Gel*, 2002, at http://www.iscpubs.com/bg/us/prod/prod1991.html.

EMBL's Proteomics Visitor Facility, Website, 2D Gel Equipment, *Protean 2D Cells from Bio-Rad*, 2001, at http://.mann.embl-heidelberg.de/Visitor_Facility/PageLinks/Instrumentation/GelchamberMain.html, and *Protean IEF Cell from Bio-Rad*, at http://www.mann.embl-heidelberg.de/Visitor_Facility/PageLinks/Instrumentation/ECellMain.html.

James R. Jefferies,, *2D Gel Electrophoresis for Proteomics Tutorial*, pp. 1-24 at http://www.aber.ac.uk/parasitology/Proteome/Tut_2D.html (last tutorial update: Jan. 7, 2003.

The Scripps Research Institute, Website, *Proteomics Module*, 2003, pp. 1-3 at http://core-eye.scripps.edu/proteomics.htm.

2D Protocols, Website, *Analysis of Proteins Using Small Format 2D Gel Electrophoresis*, 2000, pp. 1-5, at http://www.abdn.ac.uk/~mmb023/protocol.htm.

Biowire.com, Website, *The Nucleus*, 2000-2002, p. 1-4, at http://www.biowire.com/nucleus/nucleus_1_3.jsp.

Bio-Rad Laboratories, Website, *Electrophoresis*, 2003, at http:www.bio-rad.com/B2B/BioRad/produict/br_category.jsp.

* cited by examiner

DISTRIBUTED MULTI-SEGMENTED RECONFIGURABLE TRAVELING WAVE GRIDS FOR SEPARATION OF PROTEINS IN GEL ELECTROPHORESIS

TECHNICAL FIELD

The present invention relates to the field of electrophoretic separation of molecules, and, more particularly, to initial rapid transport and subsequent concentration or focusing of proteins in gel electrophoresis. The present invention also relates to analytical methods based upon the observation of the migration of particles in response to an electric field.

BACKGROUND OF THE INVENTION

Electrophoresis is a separation technique most often applied to the analysis of biological or other polymeric samples. It has frequent application to analysis of proteins and DNA fragment mixtures. The high resolution of electrophoresis has made it a key tool in the advancement of biotechnology. Variations of this methodology are used for DNA sequencing, isolating active biological factors associated with diseases such as cystic fibrosis, sickle-cell anemia, myelomas, and leukemia, and establishing immunological reactions between samples on the basis of individual compounds. Electrophoresis is an extremely effective analytical tool because it does not affect a molecule's structure, and it is highly sensitive to small differences in molecular charge and mass.

Electrophoresis in a polymeric gel, such as a polyacrylamide gel or an agarose gel, adds two advantages to an electrophoretic system. First, the polymeric gel stabilizes the electrophoretic system against convective disturbances. Second, the polymeric gel provides a porous passageway through which the molecules must travel. Since larger molecules will travel more slowly through the passageways than smaller molecules, use of a polymeric gel permits the separation of molecules by molecular size.

One common electrophoretic procedure is to establish solutions having different pH values at each end of an electric field, with a gradient range of pH in between. At a certain pH, the isoelectric point of a molecule is obtained and the molecule carries no net charge. As the molecule crosses the pH gradient, it reaches an isoelectric point and is thereafter immobile in the electric field. Therefore, this electrophoresis procedure separates molecules according to their different isoelectric points.

More specifically, this procedure is referred to as isoelectric focusing (IEF) wherein an electric field is applied to a molecule in a pH gradient to mobilize the molecule to a position in the pH gradient at which its net charge is zero, i.e., the isoelectric point of the molecule. It often is used to separate proteins in a mixture and as an aid in the characterization of biomolecules of unknown composition. Commercially available gradients maybe utilized in isoelectric focusing which consist of multicharged ampholytes, with closely spaced isoelectric values and high conductivity, which partition into a pH gradient upon application of an electric field. The ampholytes are generally provided in a support matrix, such as a polyacrylamide gel.

Because protein samples are actually ampholytes, when samples are loaded onto the gel and a current is applied, the compounds migrate through the gel until they come to their isoelectric point where they reach a steady state. Isoelectric focusing takes a long time (from about 3 to 30 hours) to complete because sample compounds move more and more slowly as they approach the pH in the gel that corresponds to their isoelectric points. Because the gradient ampholytes and the samples stop where they have no mobility, the resistivity of the system increases dramatically toward the end of the experiment, and the current decreases dramatically. For this reason, isoelectric focusing is usually run with constant voltage. Constant current application can lead to overheating of the system.

The combination of sodium dodecyl sulfate (SDS), $CH_3(CH_2)_{10}CH_2OSO_3Na$, also known as lauryl sulfate, treatment of samples and polyacrylamide gel electrophoresis was first described in the late 1960s. SDS is an ionic surfactant which solubilizes and denatures proteins. The surfactant coats a protein through hydrophobic interactions with the polypeptide backbone, effectively separating most proteins into their polypeptide subunits. The majority of proteins to which SDS binds then unfold into linear molecules having a similar surface potential.

SDS-polyacrylamide gel electrophoresis (SDS-PAGE) allows separation of molecules strictly on the basis of size, i.e., molecular weight. When SDS-treated samples migrate into a gel and are electrophoresed, the principal difference is size or length. Smaller molecules travel through the matrix more quickly than those that are larger. The rate at which molecules migrate through a polyacrylamide gel is inversely linear with the logarithm of their molecular weight. Thus denatured samples can be analyzed alongside standards of known molecular weight to aid in the interpretation of a substance's physical size.

Two-dimensional (2D) electrophoresis is unique, offering an analytical method that is both reproducible and sensitive. It is referred to as 2D because it employs two different methods of electrophoresis, in two different dimensions, to produce one result. Each method separates the sample compounds based on different properties of each compound. The combination of the two methods gives better resolution of the compounds in the sample than could be achieved with either method alone. For example, each method alone may separate up to 100 components of a sample, whereas together they may separate up to 10,000 components.

A pair of electrophoretic techniques commonly employed in 2D analyses are the previously noted isoelectric focusing (IEF) and SDS-polyacrylamide gel electrophoresis (SDS-PAGE). IEF separates sample compounds according to isoelectric point, whereas SDS-PAGE separates the compounds by molecular weight. A 2D analytical technique using IEF and SDS-PAGE to separate total protein results in a gel having bands or spots in a random pattern. Each spot represents a unique component of a sample. A single charge difference in a component can be identified on the gel by a unique spot. This property of 2D electrophoresis, which allows identification of identical proteins that differ by one charge difference, has made it an invaluable technique for the molecular genetic community.

As noted, many proteins are separated by polyacrylamide gel electrophoresis (PAGE) (based on the molecular weight) or modified polyacrylamide gel isoelectric focusing (IEF) (based on molecular charge). Both of the techniques can be used in tandem in a two-dimensional approach for maximum resolution. Polyacrylamide gels are made by polymerizing the monomer, acrylamide, into long strands, and then linking the strands together with a 'cross-linker', usually N,N'-methylene-bis-acrylamide (bis). The relative proportions of these components will determine the separation characteristics of the gel. Isoelectric focusing is carried out in a PAGE gel that contains an immobilized pH gradient consisting of high molecular weight polyaminocarboxylic acid (ampholytes). The separation power of two dimensional polyacrylamide gel electrophoresis (2D PAGE) has often been exploited as part of isolation schemes for determining the amino acid sequence of unknown proteins from complex protein mixtures.

Particles can be manipulated by subjecting them to traveling electric fields. Such traveling fields are produced by applying appropriate voltages to microelectrode arrays of suitable design. Traveling electric fields are generated by applying voltages of suitable frequency and phases to the electrodes.

This technique of using traveling electric fields relates to an important method for separation and sorting of large particles and cells referred to as dielectrophoresis. Dielectrophoresis is defined as the movement of a polarisable particle in a non-uniform electric field. Essentially, the force arises from the interaction of the field non-uniformity with a field induced charge redistribution in the separated particle.

Particles are manipulated using non uniform electric fields generated by various configurations of electrodes and electrode arrays. As a general biotechnological tool, dielectrophoresis is extremely powerful. From a measurement of the rate of movement of a particle the dielectric properties of the particle can be determined. More significantly, particles can be manipulated and positioned at will without physical contact, leading to new methods for separation technology.

A powerful extension of dielectrophoresis separation is traveling wave dielectrophoresis (TWD) in which variable electric fields are generated in a system of electrodes by applying time varying electric potential to consecutive electrodes. Such a method of Traveling Wave Field Migration was described by Parton et al. in U.S. Pat. No. 5,653,859, herein incorporated by reference. Although satisfactory, this work is not directed to the field of protein analyses and in particular, to 2D gel electrophoresis techniques.

A microfluidic device for electrophoretic separation of biomolecules such as DNA and protein was described by Dunphy et al. in "Rapid Separation and Manipulation of DNA by a Ratcheting Electrophoresis Microchip (REM)," Proceedings of IMECE2002, Nov. 17–22, 2002 New Orleans, La., No. IMECE2002-33564, herein incorporated by reference. The device utilizes thousands of electrodes along the length of a microchannel. An electrical potential is applied across the electrodes and selectively varied to separate molecules within the microchannel into two groups using a ratcheting mechanism. This mechanism does not employ traveling waves. Although directed to the separation of biomolecules, this strategy is based upon micro device technology and is not readily compatible with conventional laboratory proteomic equipment. Moreover, the strategy described by Dunphy et al. is silent with regard to applications involving 2D gel electrophoretic techniques, and more significantly, to IEF. Accordingly, a need exists for a device and technique for utilizing electrostatic traveling waves in conjunction with 2D gel electrophoresis techniques and equipment.

Two-dimensional (2D) gel electrophoresis is the acknowledged workhorse for proteomic research because it is simple, has high capacity, and is able to identify all proteins resolved on the gel when coupled with a mass spectrometer. However, lengthy process time, difficulty in resolving low-abundance proteins, and poor reproducibility, among other factors, has limited its full potential to becoming the definitive tool for proteomics. The present invention addresses many of these issues with a new instrument design and technique to reduce processing time and increase resolution by reducing band broadening with electrostatic traveling waves (TW).

BRIEF DESCRIPTION OF THE INVENTION

The present invention provides a new instrument design and methodologies to reduce processing time using electrostatic traveling waves. In addition to the conventional two-electrode design which creates linear fields in PAGE, traveling wave electrodes are embedded on one or both sides of the gel to augment or even replace existing electrodes. Traveling wave grids with a fine pitch can create significantly higher field strengths with much lower voltages. This combined field strength increases effective protein velocity significantly and reduces run time by an order of magnitude. With the use of innovative voltage patterns and waveforms, additional benefits may include reduced band broadening and minimized protein degradation, thus improving both resolution and reproducibility.

Directionality is determined by a sequential voltage pattern using a balanced multi-phase driver circuit such as a 4-phase, 3-phase, or 2-phase circuit in addition to a DC voltage bias which determines the propagation direction. Traveling waves promote rapid transport of charged proteins by using the higher fringing E fields. As noted, advantages over conventional gel setups include lower voltage (1 V compared to 200 V for PAGE and 8 KV for IEF), and much higher transport velocities (up to 10 times or more). However, band broadening occurs due to the characteristic trait of this mode of transport. In order to counter this, the present invention uses a strategy in which the proteins are loaded on the cell such that they are within reach of the fields from the traveling wave grid. Then it takes several cycles to synchronize their motion to move in step to the sweep frequency of the traveling wave signal. Once synchronized, the propagation velocity in the operating regime of interest is approximately a linear function of the sweep frequency. Unless all proteins are completely loaded at any given time, the remnants contribute to band broadening as they are transported in succeeding traveling wave cycles.

In a first aspect, the present invention provides a gel electrophoretic system for analyzing biomolecule samples. The system comprises a first plate and a second plate spaced from and maintained in a parallel relationship with the first plate. The system also comprises a gel adapted for use in electrophoretic separation of biomolecules. The gel is disposed in a layer between the first plate and the second plate. The system also comprises a traveling wave grid disposed in contact with the gel. The traveling wave grid includes a plurality of electrodes. The system additionally comprises a first voltage source in electrical communication with the traveling wave grid and providing an electrical potential between a first edge of the gel layer and a second edge of the gel layer. The system further comprises a second voltage source providing an electrical potential between a first face of the gel layer and a second face of the gel layer to promote loading of biomolecules against the traveling wave grid.

In another aspect, the present invention provides a gel electrophoretic system having a distributed multi-segmented traveling wave grid. The system comprises a layer of a gel suitable for use in gel electrophoresis of biomolecules. The system further comprises a first segment of a traveling wave grid in contact with the gel. The first segment of the grid has a first plurality of closely spaced parallel electrodes. The system also comprises a second segment of a traveling wave grid in contact with the gel. The second segment of the grid has a second plurality of closely spaced parallel electrodes. The system further comprises a voltage controller in electrical communication with at least one of the first segment and the second segment of the traveling wave grid. The voltage controller is configured to selectively provide (i) a first multi-phase electrical signal to at least one of the first segment of the grid and the second segment of the grid, and (ii) a second multi-phase electrical signal different than the first electrical signal to at least one of the first segment of the grid and the second segment of the grid.

In a further aspect, the present invention provides a process for separating various biomolecules from a sample utilizing a gel electrophoretic system. The system comprises (i) a layer of a gel suitable for electrophoresis, the gel layer being disposed between two parallel substrates, (ii) a traveling wave grid, the grid including at least a first grid segment and a second grid segment, and (iii) a voltage controller in selective electrical communication with the first grid segment and the second grid segment. The voltage controller is adapted to provide at least one multi-phase electrical signal. The process comprises a first step of depositing the sample on the layer of the gel. The process includes another step of applying a first multi-phase electrical signal from the voltage controller to at least one of the first grid segment and the second grid segment. This causes at least a portion of biomolecules in the sample to migrate in the gel. The process further comprises a step of applying a second multi-phase electrical signal from the voltage controller to at least one of the first grid segment and the second grid segment to thereby cause (i) the portion of biomolecules to further migrate in the gel or (ii) another portion of biomolecules in the sample to migrate in the gel.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Separation and identification of biomolecules such as proteins and DNA is an important step in biotechnology. In this post-genomic period, 2D gel electrophoresis is emerging as the workhorse for protein separation. The methodology is 30 years old and has seen mostly minor technology improvements. The present invention speeds up processing time by a two step approach. First, an initial separation is performed using a distributed multi-segmented traveling wave (TW) electrode grid system which is optimized for enhanced protein loading and fast transport. Second, the sub-samples of separated proteins are further refined or focused using specific purpose TW processing algorithms on the decoupled local TW grids. The primary objective of using electrostatic traveling waves is the very rapid transport possible by creating very high local E fields with low voltages using an electrode grid with a very fine pitch. Advantages over conventional gel setups include lower voltage (1 V compared to 200 V for PAGE and 8 KV for IEF), and much higher transport velocities (up to 10 times or more).

In a first preferred embodiment, the present invention provides a gel electrophoretic system comprising a thin layer of a gel medium disposed between two plates. One or more traveling wave grids extend along one or more interior faces of the plates and in contact with the gel. A first voltage source is provided and configured to apply a voltage potential across two opposite edges of the gel layer. Specifically, the first voltage source is in electrical communication with the traveling wave grid. As will be understood, the voltage potential causes biomolecules dispersed or applied to the gel, to travel from one edge toward the other edge of the gel layer. It is further preferred to provide a second voltage source and apply a voltage potential across the faces of the gel layer. The second voltage potential is preferably applied such that biomolecules in the gel layer are urged or "loaded" toward the traveling wave grid.

Figure 1A:
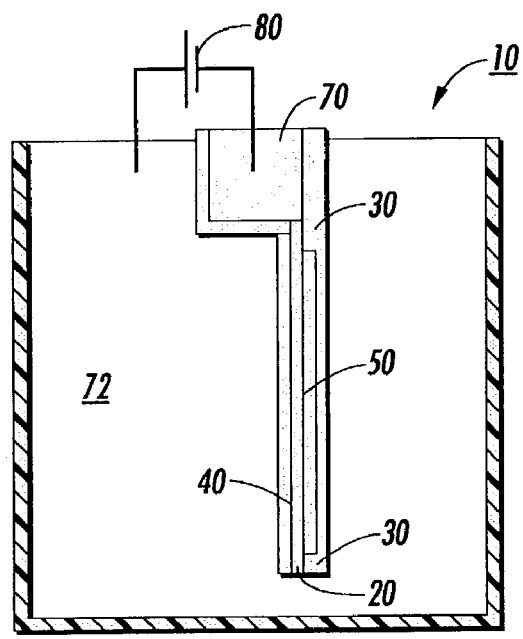
FIG. 1A is a schematic illustration of a preferred gel electrophoresis system in accordance with the present invention.

FIG. 1A is a schematic illustration of a preferred embodiment gel electrophoresis system 10 comprising a thin layer 20 of a polyacrylamide gel cast between a glass plate 30 and a Plexiglas back plate 40. Gel thickness is controlled by Teflon shims. A traveling wave grid 50 is fabricated by depositing platinum electrodes on the glass 30. A thin layer of titanium may be used to improve adhesion of the platinum to the glass. The other plate may provide another identical traveling wave grid formed on glass to thereby provide a double-sided structure. The electrode and gel assembly is placed in electrical communication with a voltage source 80. One representative assembly is to immerse the electrode and gel assembly in a suitable electrically conductive buffer solution. Inner and outer chambers, designated as 70 and 72 respectively, contain the buffer solution. As will be appreciated, an electrical circuit is formed with the voltage source 80 such that the electrode and gel assembly provide the only path for the flow of electrons through the buffer solution to and from the voltage source 80. In addition, buffer solution in the outer chamber 72 also serves to cool the electrode and gel assembly immersed therein. The advantage of utilizing traveling wave grids on both sides of the gel is to either double the in-plane E fields for the same gel thickness, or double the gel thickness for the same E field. The latter may be especially useful if the protein packing capacity of the gel is important in order to attain a minimum level for sample detection. The ionic buffer such as the two buffer solutions in chambers 70 and 72 of FIG. 1A, serve as the two electrodes across which a DC field is applied. The protein sample is typically loaded onto the top of the gel and the electrophoretic current is forced to flow through the gel. In SDS-PAGE operation, the proteins or biomolecules in the sample migrate within the gel according to their molecular weight; with the lightest molecules migrating the furthest distance. In the schematic illustration of FIG. 1A, the migrating proteins flow downward through the layer 20 of gel.

Figure 1B:
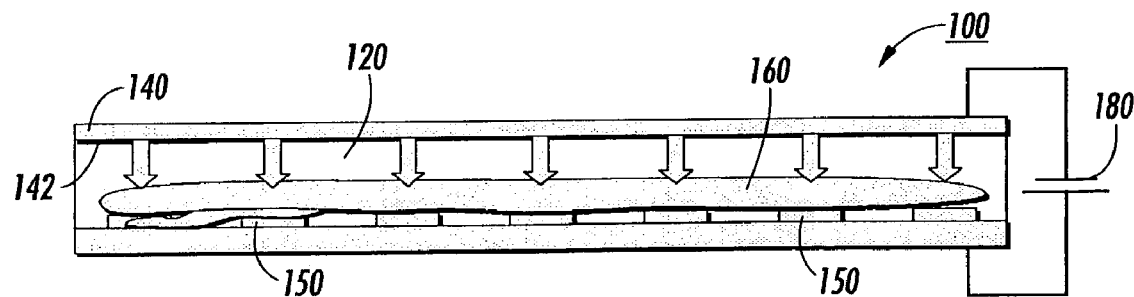
FIG. 1B is a schematic illustration of another preferred gel electrophoresis system in accordance with the present invention.

Another preferred embodiment system as shown in FIG. 1B, utilizes a Plexiglas back plate 140 with a thin 200 Angstrom layer of platinum deposited on the inside face 142 of the plate 140 to contact the gel 120. A voltage source 180 is provided in electrical communication with the resulting electrode and gel assembly. The platinum forms a counter electrode for electrostatic pressure to load the proteins 160 against a traveling wave grid 150 so as to enhance protein loading as shown in FIG. 1B. For a 100 um thickness gel layer, only −0.1 V is sufficient to provide the necessary electrostatic pressure for SDS treated negative proteins. This voltage is below the threshold of significant gas formation. It is contemplated that the embodiment of FIG. 1B for "loading" the proteins against the grid, may be used in conjunction with the embodiment of FIG. 1A.

Figure 2A:
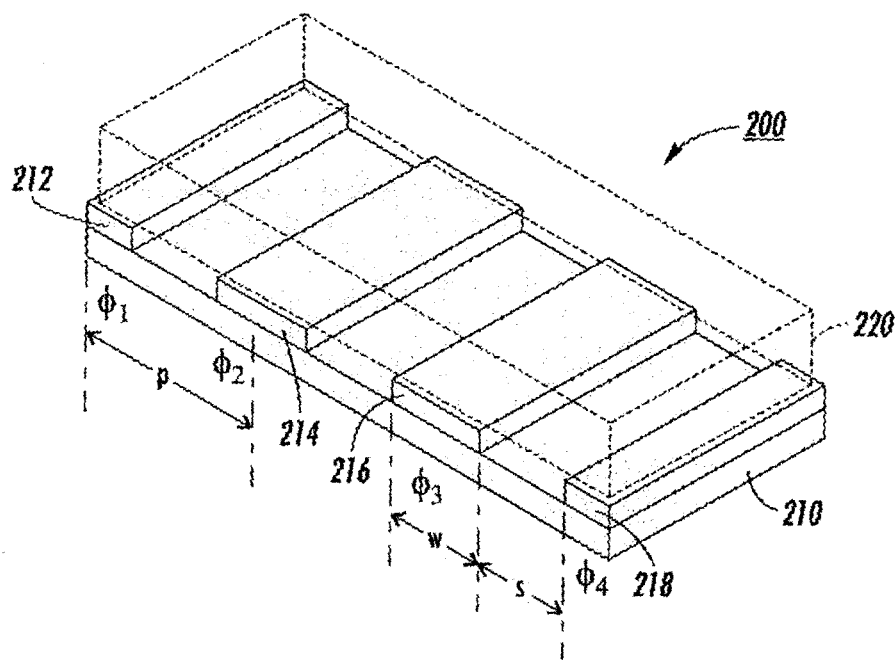
FIG. 2A is a schematic illustration of a preferred single sided traveling wave grid configuration with gel, in accordance with the present invention.
Figure 2B:
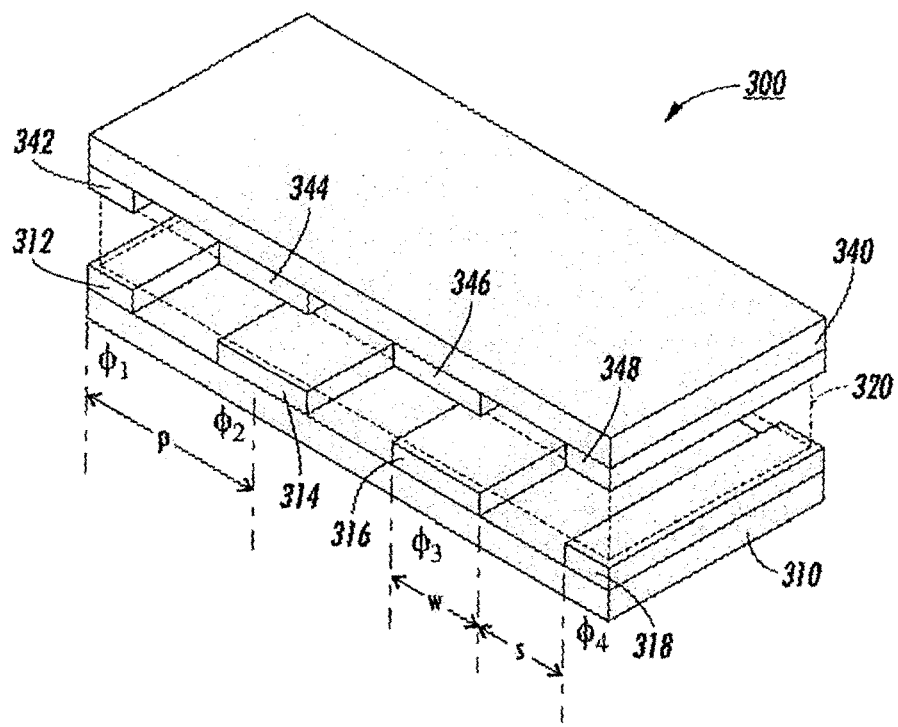
FIG. 2B is a schematic illustration of a preferred double sided traveling wave grid configuration with gel, in accordance with the present invention.

FIGS. 2A and 2B are schematic illustrations of preferred embodiment single and double sided traveling wave grid assemblies. The assemblies include an effective amount of a gel disposed in intimate relation thereto. Specifically, FIG. 2A is a single sided grid assembly 200 comprising a plate 210, a plurality of parallel and closely spaced electrodes 212, 214, 216, and 218, and an effective amount of a gel 220 in electrical communication with the electrodes. Most preferably, the electrodes are formed from platinum or alloys thereof. It is also preferred to deposit a thin layer of titanium on the plate, which is preferably glass, to promote adhesion between the electrodes and plate. As described herein, it is preferred to utilize a four (4) phase electrical signal in conjunction with the preferred embodiment systems, assemblies, and grids noted herein. Accordingly, it is preferred that a first electrode such as electrode 212 be utilized for a first phase $\phi_1$, of the electrical signal. Similarly, it is preferred that a second electrode immediately adjacent to the first, such as electrode 214, be utilized for a second phase $\phi_2$ of the electrical signal. And, it is preferred that a third electrode immediately adjacent to the second electrode, such as electrode 216, be utilized for a third phase $\phi_3$ of the electrical signal. Moreover, it is preferred that a fourth electrode immediately adjacent to the third electrode, such as electrode 218, be utilized for a fourth phase $\phi_4$ of the electrical signal. As described in greater detail herein, the distance between the centers of adjacent electrodes is referred to as pitch, and denoted as "p." The width of an electrode is denoted as "w." And the distance between facing sidewalls or edges of adjacent electrodes is "s."

FIG. 2B is a schematic illustration of a preferred double sided traveling wave grid assembly 300 comprising a first plate 310; a first plurality of parallel and closely spaced electrodes 312, 314, 316, and 318; a second plate 340; a second plurality of parallel and closely spaced electrodes 342, 344, 346, and 348; and an effective amount of a gel 320 in electrical communication with the first and second plurality of electrodes.

Figure 3:
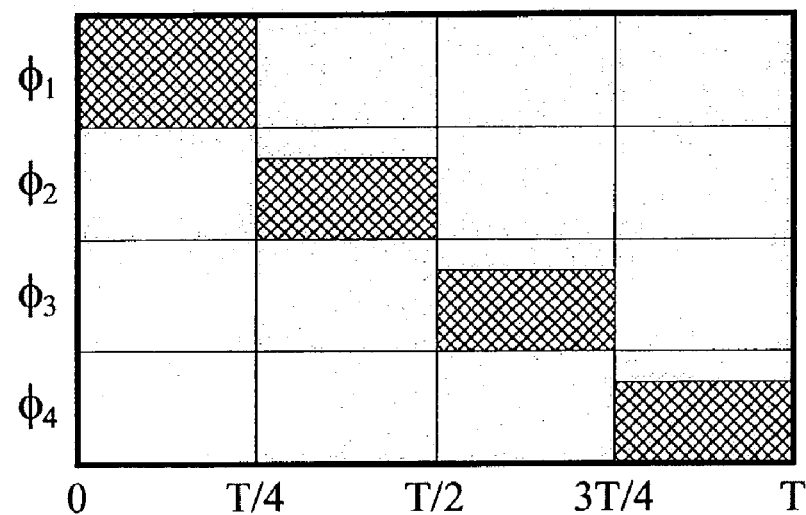
FIG. 3 is a representative four phase traveling wave voltage pattern employed in the preferred systems and traveling wave grids of the present invention.
Figure 4:
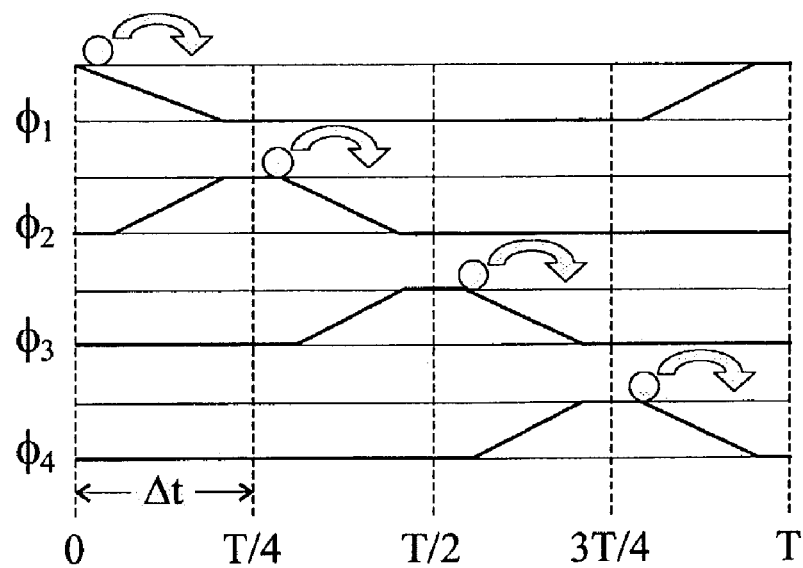
FIG. 4 is a schematic illustration of biomolecule transport from one electrode to another.

FIG. 3 is a representative four phase voltage pattern or waveform used in the preferred embodiment systems and traveling wave grids of the present invention. Specifically, FIG. 3 depicts the four phase voltage waveform with 90 degree separation between phases. Each waveform occurring in each phase is a square wave pulse. Each pulse is sequentially applied to an adjacent electrode. Thus, a first pulse in phase $\phi_1$, is applied to a first electrode for a desired time period, such as T/4. Upon completion of that first pulse, such as at time T/4, a second pulse in phase $\phi_2$ is applied to a second electrode, preferably immediately adjacent to the first electrode. Upon completion of that second pulse, such as at time T/2, a third pulse in phase $\phi_3$ is applied to a third electrode, preferably immediately adjacent to the second electrode. Upon completion of that third pulse, such as at time 3T/4, a fourth pulse in phase $\phi_4$ is applied to a fourth electrode, preferably immediately adjacent to the third electrode. This sequential and ordered array of voltage pulsing results in biomolecules dispersed in the gel to "hop" from the vicinity of one electrode to another. The synchronous mode of propagation is depicted in FIG. 4 and may be described as a "hopping" mode where the biomolecules or proteins hop from electrode to electrode in the direction of the pulse train. The transit time to migrate across the dielectric space is then given by:

$$t_{transit} = s/\mu E,$$

where pitch is given by p=w+s, and w and s are the electrode width and dielectric space, respectively. Electric field and mobility are given by E and µ, respectively. The period for one cycle through the 4-phases is $4*t_{transit}$, so that the maximum sweep frequency is:

$$f \leq \mu E/4s.$$

For sustained transport, the protein has to have sufficient speed (µE) and time ($t_{transit}$) to traverse the distance of the dielectric space, s. This equation implies that for sustained transport, there is a critical frequency for proteins of a certain mobility. Therefore, by starting with the highest operational frequency, one can progressively scan downwards in frequency until the protein of the right mobility starts to move. This means that the fastest (and lowest molecular weight) proteins may be separated out from the sample of biomolecules one at a time.

Figure 5:
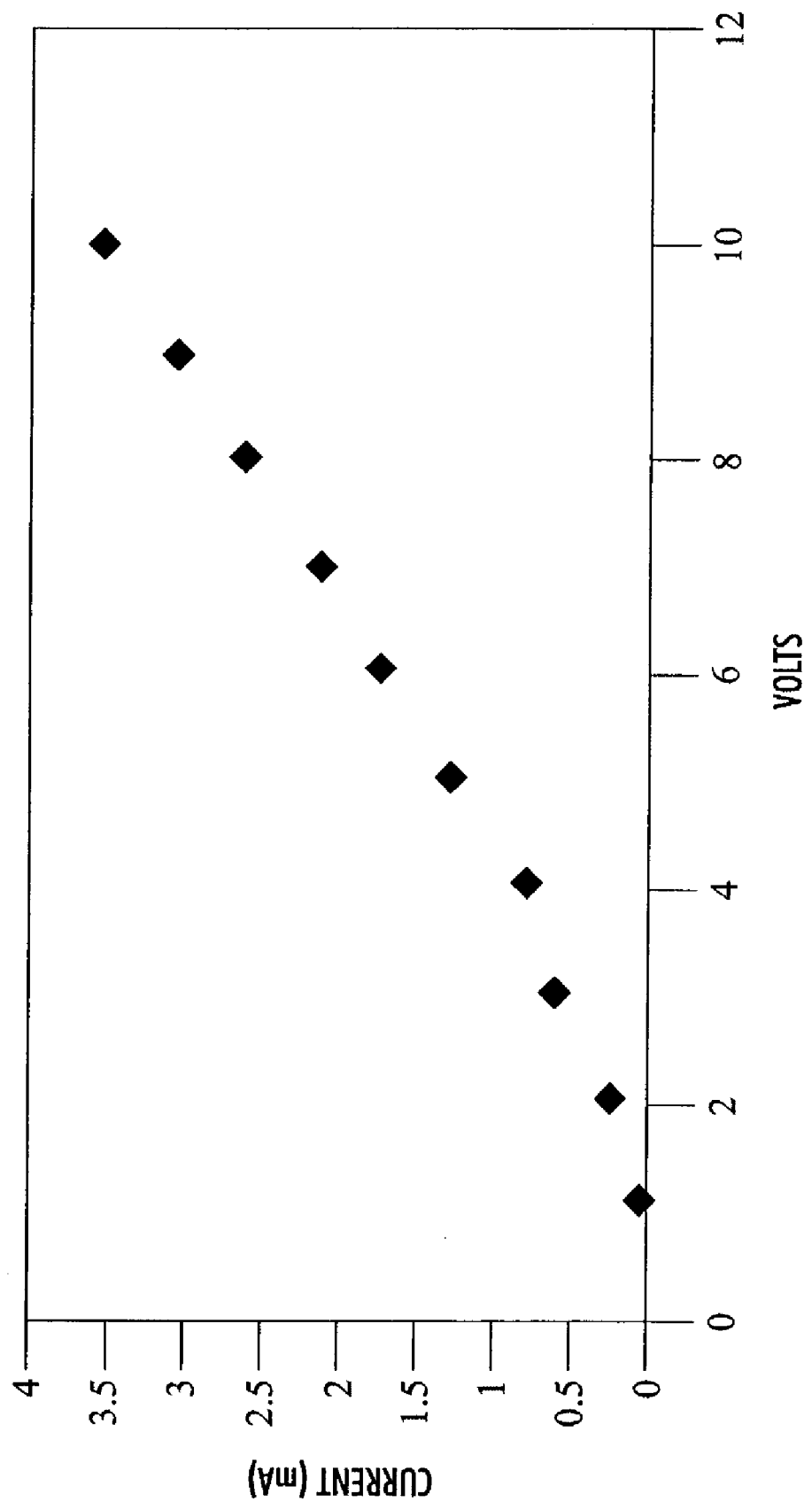
FIG. 5 is a graph illustrating the onset of hydrolysis in a system utilizing platinum on glass electrodes.

Speed improvements compared to conventional gel electrophoresis are shown in Table 1, below. One objective of the present invention is to operate at a voltage below the threshold of significant gas formation. This means staying below 1.5–2 V, a number determined from measurement and confirmed by theory. It will be appreciated that the maximum voltage depends upon a host of factors including system parameters and the biomolecules present. FIG. 5 illustrates the onset of hydrolysis at various current and voltage levels in a system utilizing platinum on glass electrodes. The traveling wave electrodes operate in direct contact with the gel and ions in the buffer to avoid the Debye double-layer shielding of the grids. Some hydrolysis will take place resulting in non-zero net current. The normal DC bias typically applied between the two extreme edges of the gel may also be used to initially load the proteins into the gel and to move them onto the traveling wave grid. In fact, these two electrodes may also serve as backup hydrolysis electrodes, remote from the gel, at which the required level of electrophoretic current is attained.

biomolecules, a multi-segmented system of traveling wave grids, and a voltage controller in electrical communication with said grids. Each of the grid segments includes a plurality of closely spaced parallel electrodes that are in contact with the gel. The voltage controller is adapted to provide one or more selectable multi-phase electrical signals to one or more of the grid segments. In a particularly preferred embodiment, the voltage controller provides a first multi-phase electrical signal to at least one of the grid segments and a second multi-phase electrical signal to all or only some of the grid segments. In still other preferred aspects, the system may comprise two, three, or more voltage controllers that may be configured to provide one or more particular multi-phase electrical signals to one or more grid segments of the traveling wave grid.

TABLE 1

TRAVELING WAVE SYNCHRONIZATION PARAMETERS
PAGE conditions: 200 V over 8.5 cm for 65 minutes
Effective $\mu = 0.9274 \times 10^{-4}$ cm$^2$/V · s

| Parameter Set | p um | s um | $\Delta$V V | Max E V/um | Min $t_{transit}$ S | Min T S | Max f Hz | Max v um/s |
|---|---|---|---|---|---|---|---|---|
| a | 200 | 100 | 0.235 | $2.350 \times 10^{-3}$ | 9.1743 | 36.6972 | 0.0273 | 21.8 |
| b | 200 | 100 | 1.0 | $10.00 \times 10^{-3}$ | 2.1564 | 8.6254 | 0.1159 | 92.75 |
| c | 200 | 100 | 2.0 | $20.00 \times 10^{-3}$ | 1.0782 | 4.3127 | 0.2319 | 185.5 |
| d | 40 | 30 | $70.50 \times 10^{-3}$ | $2.350 \times 10^{-3}$ | 1.8349 | 7.3394 | 0.1363 | 21.8 |
| e | 40 | 30 | 1.0 | $33.33 \times 10^{-3}$ | 0.1294 | 0.5176 | 1.9319 | 309.10 |

In Table 1, p is the pitch of the electrode grid. The designation s is the spacing between electrodes. $\Delta$V is the voltage potential of an electrical signal applied to an electrode. Max E is the maximum propagating electrical field extending about an electrode as a result of the voltage signal applied thereto. Min $t_{transit}$ is the transit time for a biomolecule to travel a distance of 1 pitch. This is also equivalent to one-quarter of the time of one period of the electrical signal. Min T is the time of one period of the electrical signal. Max f is the frequency of the electrical signal. Max v is the maximum velocity of propagation of biomolecules within the system.

Table 1 also reveals several preferred combinations of traveling wave grid dimensions, voltage bias, corresponding sweep frequency and predicted idealized maximum velocities. The estimated velocities are upper estimates since such estimates assume that the E field is entirely planar. The actual velocity value will be smaller by a factor of 2 to 3 times. The first parameter set a is consistent with a typical commercial setup from Bio-Rad. To achieve the same processing time, a 200 um pitch traveling wave grid would need to be biased at 0.235V with a sweep frequency lower than 0.02373 Hz. However, if the voltage is raised to 1V, as in set b, the frequency can be increased to 0.115 Hz and the peak velocity is now about 4 times higher. When a smaller pitch is used as shown in sets d and e, the local E field is even much higher so that up to 14 times velocity increase is possible at 1V bias. Since PAGE typically runs for 65 minutes, the use of traveling waves would result in a significant reduction in process time to a matter of minutes over an 8.5 cm Criterion 2D gel.

Figure 6:
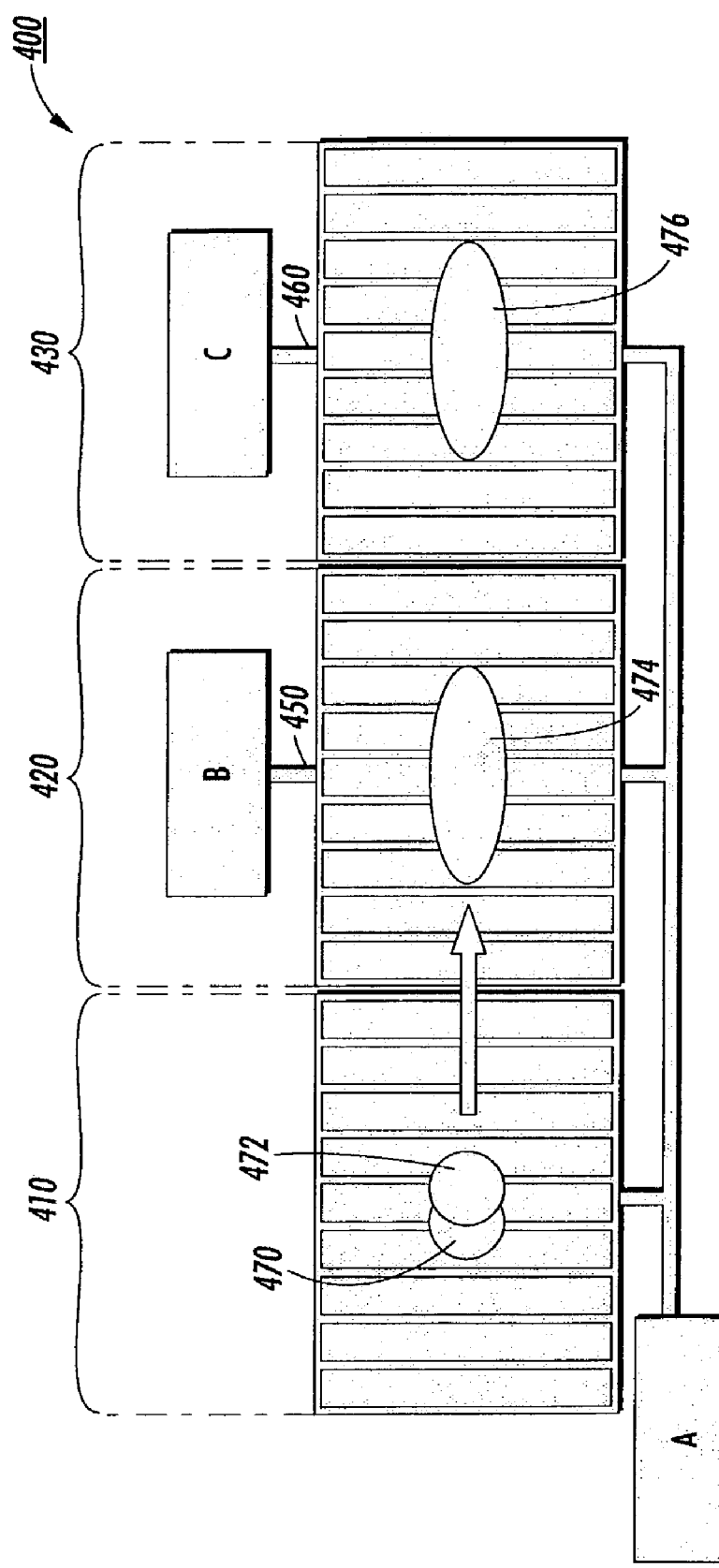
FIG. 6 is a schematic illustration of a preferred embodiment gel electrophoretic system utilizing distributed, reconfigurable, and reprogrammable traveling wave grids in accordance with the present invention.

In another preferred embodiment, the present invention provides a gel electrophoretic system having a distributed multi-segmented traveling wave grid. The system includes a layer of a gel suitable for use in gel electrophoresis of The present invention provides significant opportunity for innovation in the design of specific waveforms to focus, separate, and concentrate proteins. One preferred strategy is to fabricate the smallest pitch possible for the traveling wave grids for maximum flexibility in reconfiguring them for specific applications. FIG. 6 is a schematic illustration of a preferred embodiment gel electrophoretic system 400 utilizing multiple distributed, reconfigurable, and reprogrammable traveling wave grids. Specifically, FIG. 6 shows a preferred multi-segmented traveling wave grid system. The preferred multi-segmented traveling wave grid system includes a first grid segment 410, a second grid segment 420, and a third grid segment 430. As will be appreciated, each segment includes a plurality of parallel and closely spaced electrodes. Two contiguous pads on respective sides together offer connection to the 4 phase circuit through one or more busses 440, 450, and 460. The system 400 preferably further includes one or more programmable voltage controllers such as controllers A, B, and C depicted in FIG. 6. As will be appreciated, the controllers are in electrical communication with the traveling wave grid (or segments thereof) through the noted busses.

In utilizing the preferred embodiment system 400, one particularly preferred strategy involves moving proteins of interest onto individual local traveling wave grid segments using controller A where they are then available for subsequent processing using controllers B, C and so forth. Each controller may be a separate PIC implementation or a single PIC with multiple pre-programmed instructions. For example, in operation, the preferred embodiment system 400 of FIG. 6 may be utilized to separate a sample of various biomolecules as follows. A sample 470 is deposited onto the grid segment 410. The sample migrates to region 472 and continues to migrate onto adjacent grid segment 420. Operation of system 400 continues until a region 474 of biomolecules forms within grid 420. Depending upon the biomolecules and grid parameters, the biomolecules constituting region 474 may further migrate to adjacent grid segment 430, and form a region 476 of biomolecules. Generally, this strategy utilizes an initial separation using a first controller and secondary refinements or further separation using other controllers and segments of grids. Secondary refinements include further concentrating of migrated biomolecules and focusing of bands or patches.

In still another preferred embodiment, the present invention provides a process for separating various biomolecules from a sample. The process utilizes a gel electrophoretic system comprising a layer of a gel suitable for electrophoresis, the layer being disposed between two co-planar substrates. The system also includes a traveling wave grid which includes at least a first grid segment and a second grid segment. The system additionally includes a voltage controller in selective communication with the first grid segment and the second grid segment. The process comprises a first step of depositing the sample of biomolecules on the layer of the gel. Next, a first multi-phase electrical signal, such as a four phase electrical signal, is applied to one or both of the first and second grid segments. This causes at least a portion of the biomolecules in the sample to migrate in the gel. A second multi-phase electrical signal is applied to one or both of the first and second grid segments to further cause either the same portion of biomolecules to further migrate in the gel or another portion of biomolecules in the sample to migrate in the gel. By selectively applying appropriate multi-phase electrical signals to one or both of the grid segments, the sample can be selectively analyzed or separated.

If the system utilizes multiple voltage controllers, the process can further apply one or more multi-phase electrical signals generated by those additional controllers to various grid segments as desired. Additionally, each of the various voltage controllers used in this system may be configured to provide varying or changing multi-phase electrical signals. Changes in these signals may include changes in voltage levels, frequency, or other electrical parameters. Additionally, the present invention includes processes in which the interface between a voltage controller and one or more of the traveling grids is changed. For instance, a multi-phase electrical signal may be applied to a particular array of electrodes in a grid. After a desired stage of the separation process has been reached, the electrodes to which the multi-phase electrical signal is applied are changed. This strategy may be used to selectively analyze and separate a wide array of biomolecules in a sample.

Figure 7:
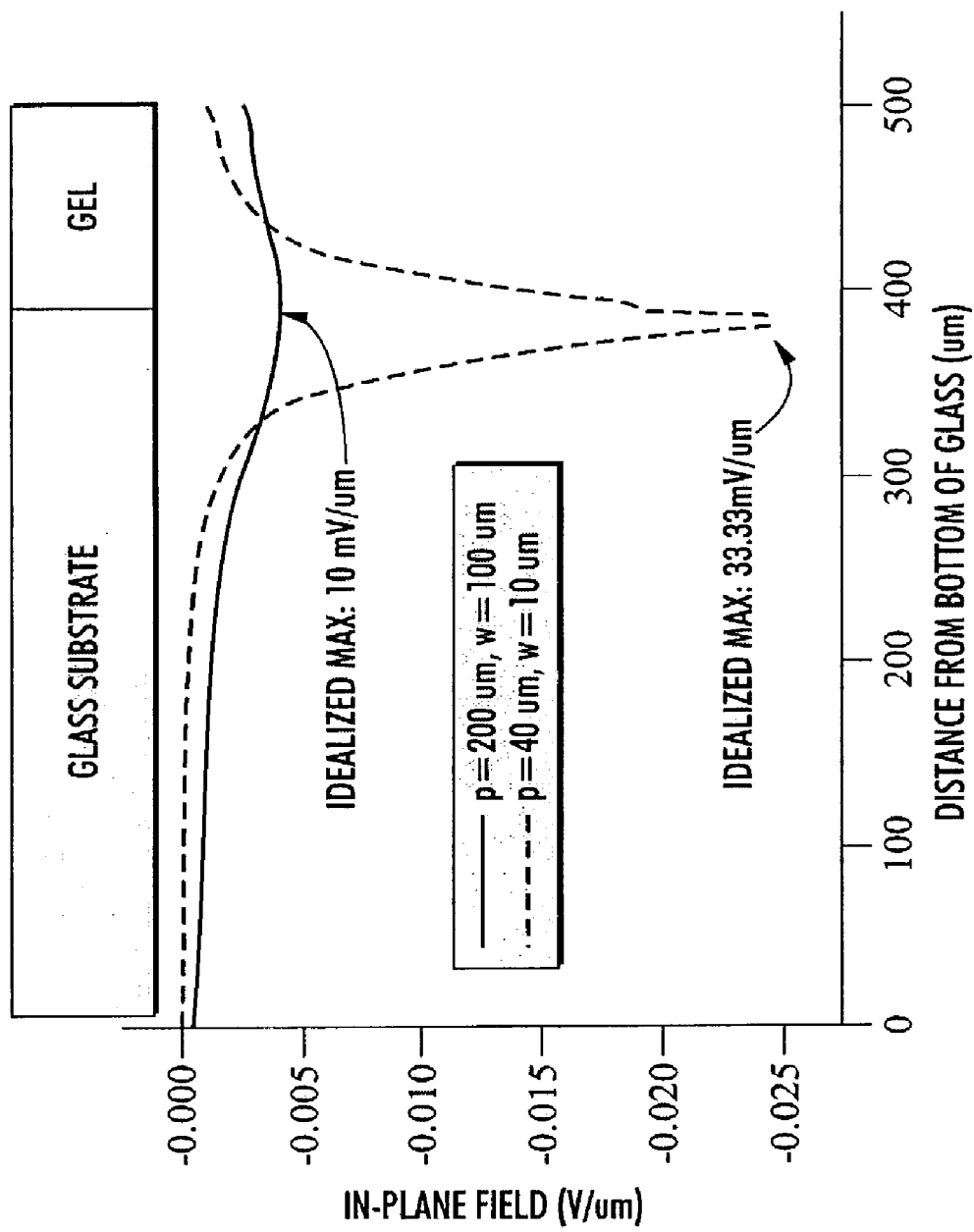
FIG. 7 is a graph illustrating the relationship between the in-plane electrical field and electrode dimensions.

Transport velocity increases linearly with decreasing pitch, so very fast transport is possible if the proteins are available in sufficient quantities and can be loaded efficiently. FIG. 7 shows the significantly higher planar E fields in the inter-electrode spacing for a traveling wave grid having a 40 µm pitch compared to a grid having a 200 µm pitch. That is, significantly higher E fields are achievable using the same voltage (1 V) when utilizing a 40 µm pitch as compared to a 200 µm pitch. Optimally, electrode width, w, is minimized, to maximize in-plane E field components in the inter-electrode spacing, s. Coarser effective pitch can be achieved by careful reconnection and floating of the appropriate contact pads. For example, an effective doubling of the fundamental spatial pitch is attained by skipping the even numbered phases in each 4-phase group. Only the odd pads are addressed. The even pads are left to float. The effective pitch is tripled when a 3-group set is considered. Here, electrodes 1 and 4 in group 1, 3 in group 2 and 2 in group 3 are driven as the new 4-phase circuit. The remaining electrodes are left to float. Dimensional optimization is performed to determine the optimal thickness of the gel to conform to the pitch of the traveling wave grids. The present invention encompasses a wide array of various combinations of electrode and grid configuration.

Figure 8:
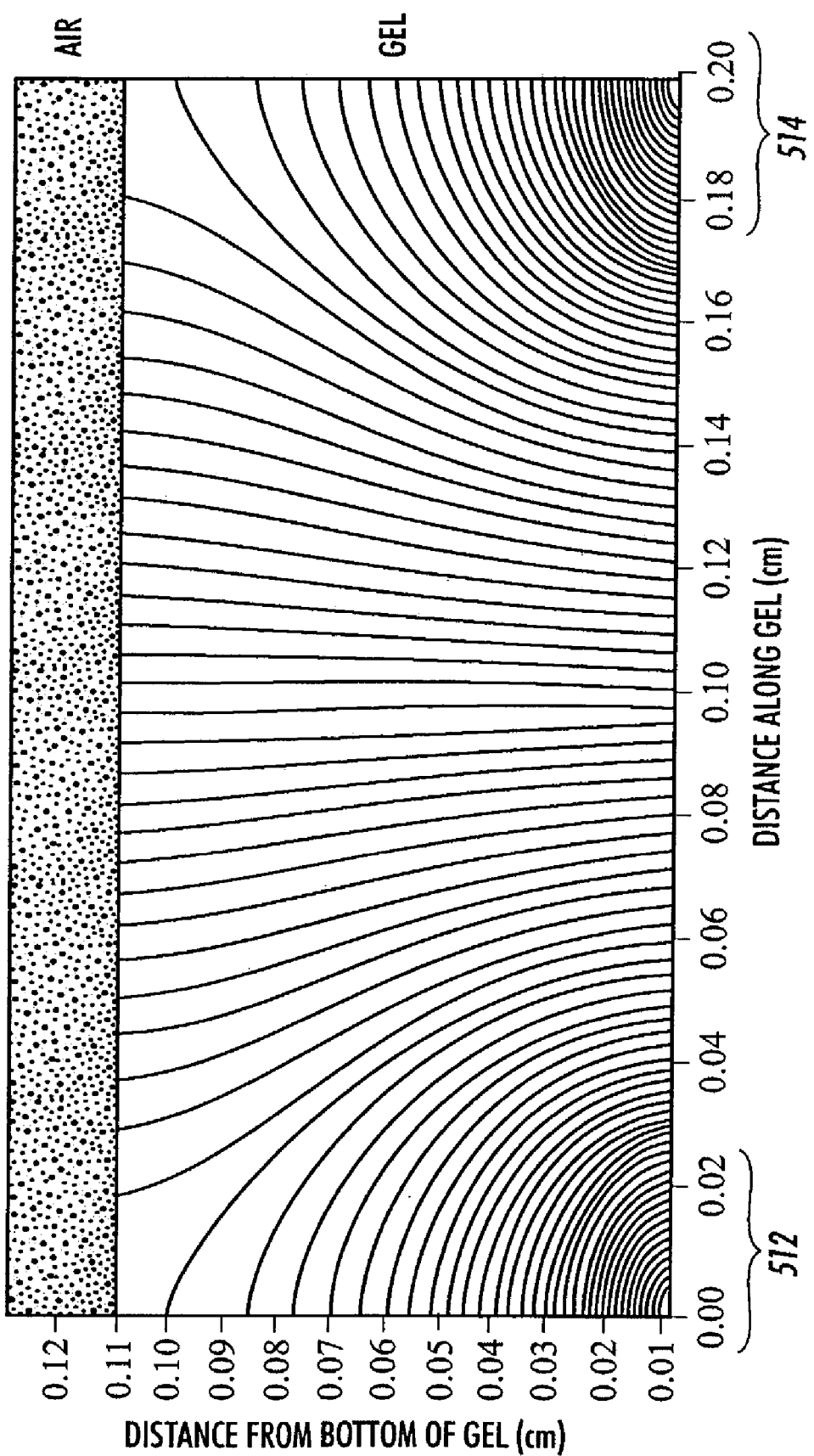
FIG. 8 is a graph illustrating electrical potential contours between two adjacent electrodes in a preferred traveling wave grid in accordance with the present invention.

FIG. 8 is a graph illustrating the E field or the electrical potential contour lines between two adjacent electrodes in a preferred traveling wave grid in accordance with the present invention. FIG. 8 depicts the E contour lines between two electrodes 512 and 514 having a pitch of 0.20 cm. The gel has a thickness of 0.11 cm. Accordingly, in this configuration, the ratio of gel thickness to pitch is approximately ⅝ from the simulation as shown in FIG. 8. This means that a typical commercial off the shelf gel which is minimally 750 µm, is too thick and generally undesirable. Very thin 100 µm polyacrylamide gels have been cast in accordance with the present invention and have been successfully used for protein separation. The use of the bias voltage on the counter plate is especially important in order to effectively load proteins onto the traveling wave grid. For much higher E fields and therefore faster speeds, a smaller pitch is needed and correspondingly thinner gels. It is expected that thin gels may be used in special cases when specific information on a small and refined protein sample is needed. In the 10 µm regime, spin coating maybe a suitable technology for forming thin layers of gel.

Figure 9:
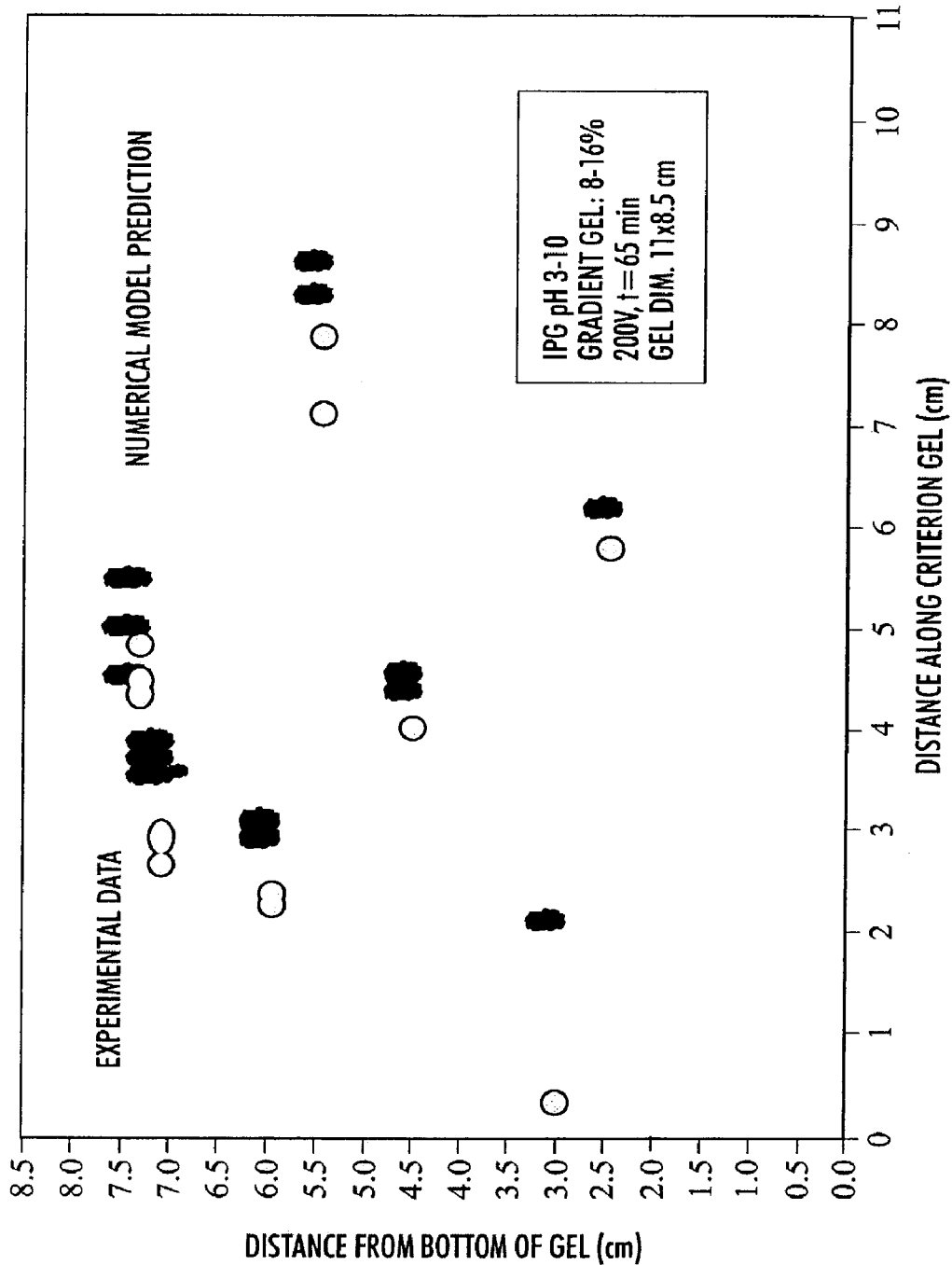
FIG. 9 is a graph illustrating a comparison between predicted and actual locations of biomolecules separated in a preferred embodiment system in accordance with the present invention.

Initial proof of concept has been attained through both experimentation and modeling. A particle model has been developed for the IEF and SDS-PAGE separation, and validated against bench data for two sets of sample proteins: a Bio-Rad protein standard, and four reference proteins from published literature. The experimental data on migration distance as a function of molecular weight is used to extract effective mobility for use in the model. Traveling wave fields are then simulated and applied to the mobility model to predict protein transport. FIG. 9 shows protein locations on a 2D Criterion gel after IEF and SDS-PAGE. The 2D protein Standard from Bio-Rad is used. Experimental data is shown as open or "white" regions, and simulation predictions are shown as darkened regions. Relatively close correlation is evident in the vertical migration axis. Lateral discrepancies may be due to a combination of gel swelling, handling, and non-uniform pH gradient along the immobilized pH gradient (IPG) strip. Through simulation, it has been established that positive voltages lead to smaller band broadening than negative voltages for PAGE separation.

Figure 10A:
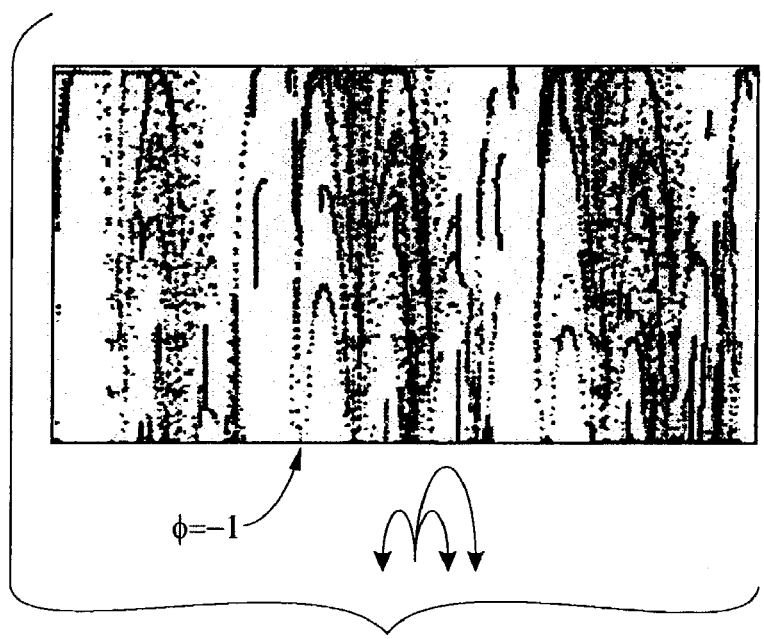
FIG. 10A is an illustration of dispersive action of biomolecules undergoing migration in accordance with the present invention.
Figure 10B:
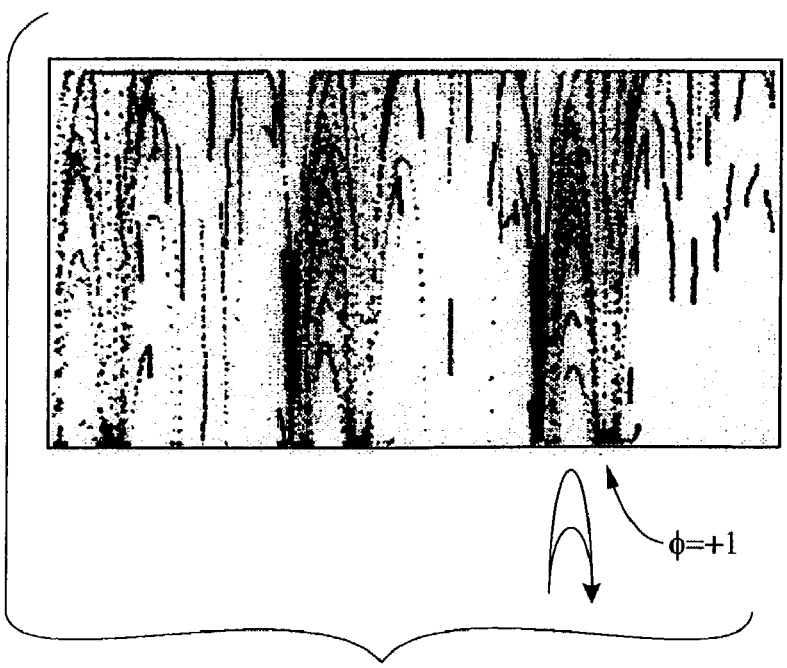
FIG. 10B is an illustration of collective action of biomolecules undergoing migration in accordance with the present invention.

FIGS. 10A and 10B illustrate the modes of transport with both negative and positive traveling wave voltages. Specifically, FIG. 10A illustrates a dispersive action in which a negative voltage wave form tends to repel biomolecules from three electrodes in a four phase group. That is, it is believed that in this configuration, biomolecules are ejected from one electrode to the other three. FIG. 10B illustrates a collective action in which a positive voltage wave form tends to attract biomolecules primarily from previous electrodes in a four phase group. That is, it is believed that in this configuration, biomolecules are essentially gathered, thereby minimizing band broadening. The shorter one-step hop for the positive voltage wave form results in less band dispersion and faster transport velocities. The use of collective action is believed to result in a more efficient capture of the biomolecules by traveling waves.

Figure 11A:
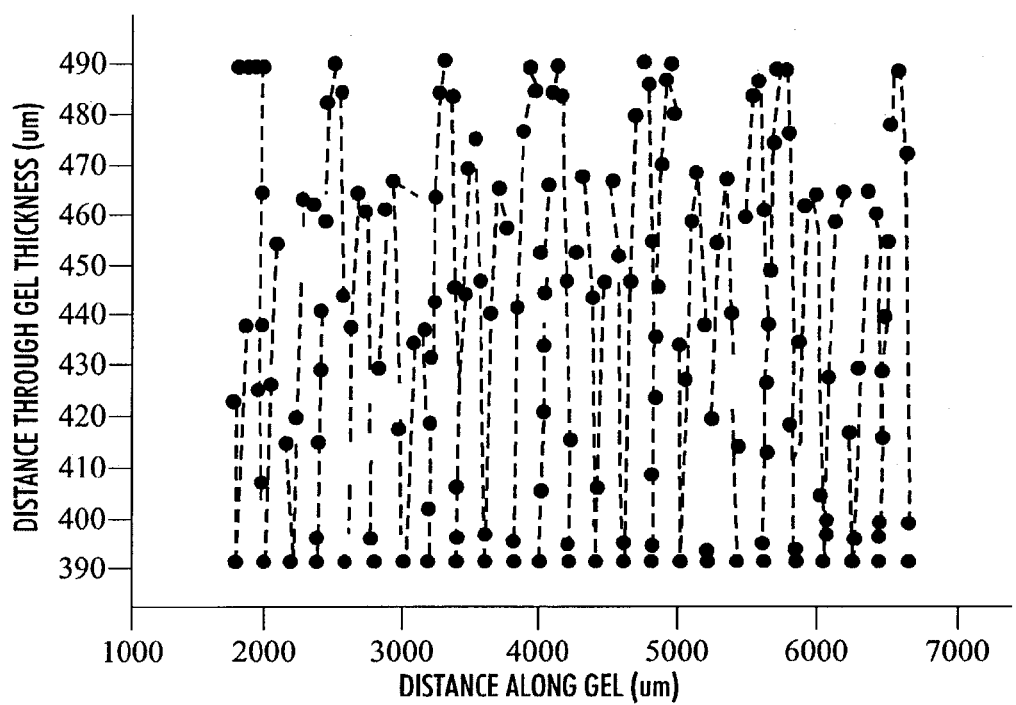
FIG. 11A is a graph illustrating biomolecule trajectory through a preferred gel electrophoretic system in accordance with the present invention.
Figure 11B:
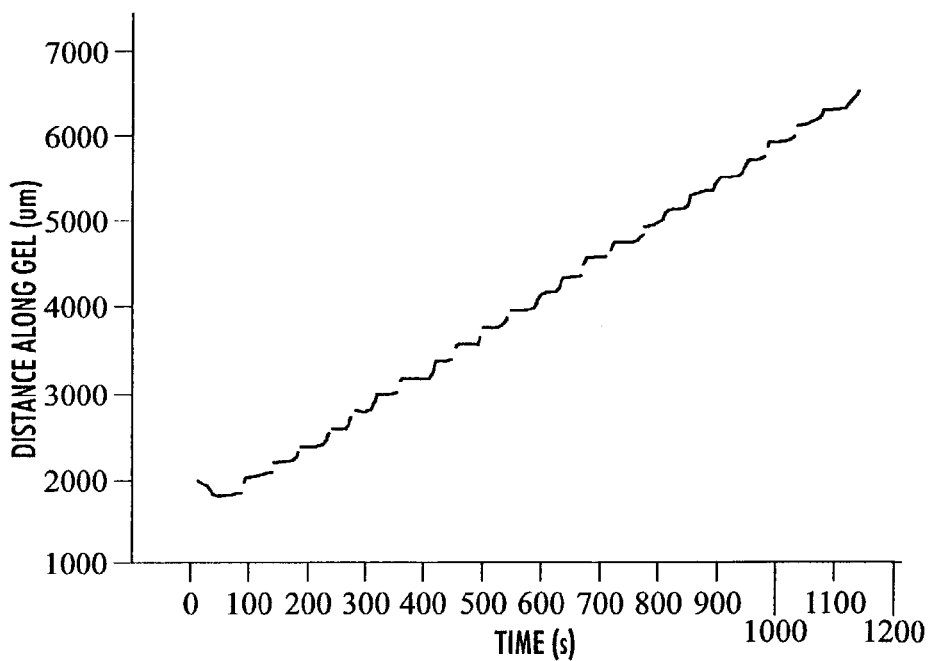
FIG. 11B is a graph illustrating the distance as a function of time traveled by the biomolecule, whose trajectory is depicted in FIG. 11A.

FIG. 11A shows the trajectory of a random protein as it hops in the direction of travel. FIGS. 11A and 11B are based upon an electrode assembly having a traveling wave grid with a pitch of about 200 µm, a width of about 100 µm, and an operating voltage of 1V. FIG. 11B shows the migration of the protein as a function of time. Again the hopping mechanism is reflected in FIG. 11B. The slope of the line in FIG. 11B provides a measure of the propagation velocity of the protein.

Figure 12:
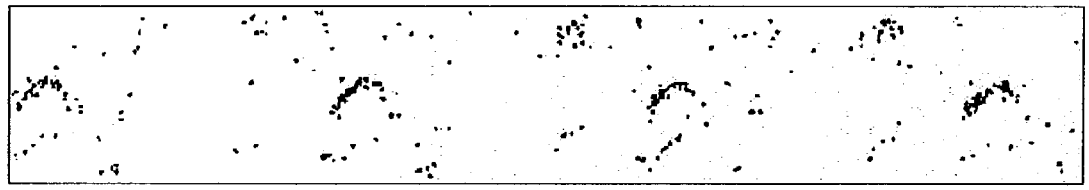
FIG. 12 is a graph illustrating groups of biomolecules migrating across a traveling wave grid in accordance with the present invention.

Another interesting aspect is that protein distribution during transport shows a feature unique to each four phase group of electrodes. FIG. 12 illustrates a snapshot in time of the protein cloud in transit between two adjacent electrodes in a four phase group. Consequently, it may be understood that the spatial resolution (or smallest resolvable feature) of the protein is given by np where n is the number of phases. Therefore, to improve this resolution, it is contemplated to reduce the number of phases to three and use a very fine pitch.

Although a wide array of configurations, arrangements, and dimensions may be used for the electrodes and electrode grids described herein, several representative aspects are as follows. The electrode pitch preferably is in the range of from about 600 µm to about 10 µm, and more preferably from about 200 µm to about 40 µm. The spacing between opposing edges of adjacent electrodes is preferably from about 300 µm to about 7.5 µm and more preferably from about 100 µm to about 30 µm. The preferred voltage level applied to the grid and electrodes is from about 5 V to about 0.001 V, and more preferably about 2 V to about 0.10 V. The preferred frequency of the electrical signal depends upon the biomolecules to be migrated, however frequencies in the range of from about 0.001 to about 10 Hz have been found useful, with preferred frequencies being from about 2 to about 0.020 Hz.

A wide array of commercially available electrophoretic equipment maybe modified or retrofitted in accordance with the present invention. Gel electrophoretic systems and cells, IPG strips, power sources, and controllers therefore may be obtained from one or more of the following suppliers: Proteome Systems Limited; Bio-Rad Laboratories; AMRESCO, Inc.; Invitrogen Corp.; Owl Separations Systems; R. Shadel Inc.; Stratagene; Zaxis, Inc.; and Amersham Biosciences.

The invention has been described with reference to the preferred embodiments. Obviously, modifications and alterations will occur to others upon reading and understanding the preceding detailed description. It is intended that the invention be construed as including all such modifications and alternations insofar as they come within the scope of the appended claims or the equivalents thereof.

What is claimed is:

1. A gel electrophoretic system for analyzing biomolecule samples, said system comprising:
    a first plate and a second plate spaced from and maintained in a parallel relationship with said first plate;
    a gel adapted for use in electrophoretic separation of biomolecules, said gel disposed in a layer between said first plate and said second plate;
    a traveling wave grid disposed in contact with said gel, said traveling wave grid including a plurality of electrodes;
    a first voltage source in electrical communication with said traveling wave grid and providing an electrical potential between a first edge of said gel layer and a second edge of said gel layer; and
    a second voltage source providing an electrical potential between a first face of said gel layer and a second face of said gel layer to promote loading of biomolecules against said traveling wave grid.

2. The system of claim 1 wherein said traveling wave grid has a pitch of from about 600 µm to about 10 µm, and a dielectric space of from about 300 µm to about 7.5 µm.

3. The system of claim 1 wherein said plurality of electrodes are formed from platinum.

4. The system of claim 1 wherein a thin layer of titanium is disposed between said first plate and said traveling wave grid.

5. The system of claim 1 further comprising:
    a second traveling wave grid also disposed in contact with said gel and including a second plurality of electrodes.

6. The system of claim 1 wherein said first voltage source provides a multi-phase electrical signal.

7. A gel electrophoretic system having a distributed multi-segmented traveling wave grid, said system comprising:
    a layer of a gel suitable for use in gel electrophoresis of biomolecules;
    a first segment of a traveling wave grid in contact with said gel, said first segment of said grid having a first plurality of closely spaced parallel electrodes;
    a second segment of a traveling wave grid in contact with said gel, said second segment of said grid having a second plurality of closely spaced parallel electrodes; and
    a voltage controller in electrical communication with at least one of said first segment and said second segment of said traveling wave grid;
    wherein said voltage controller is configured to selectively provide (i) a first multi-phase electrical signal to at least one of said first segment of said grid and said second segment of said grid, and (ii) a second multi-phase electrical signal different than said first electrical signal, to at least one of said first segment of said grid and said second segment of said grid.

8. The system of claim 7 further comprising:
    a second voltage controller in electrical communication with at least one of said first segment and said second segment of said traveling wave grid.

9. The system of claim 8 wherein said second voltage controller is configured to selectively provide a third multi-phase electrical signal to at least one of said first segment of said grid and said second segment of said grid.

10. The system of claim 7 wherein said first segment of said grid is selectively combinable with said second segment of said grid.

11. The system of claim 7 wherein said layer of said gel defines a first face and a second face opposite from said first face, said first segment of said grid being in contact with said first face of said layer of said gel, said system further comprising:
    a third segment of a traveling wave grid in contact with said second face of said layer of said gel, said third segment disposed opposite from said first segment.

12. The system of claim 7 wherein said layer of said gel defines a first face and a second face opposite from said first face, said system further comprising:
    a first electrically conductive layer disposed along said first face of said gel;
    a second electrically conductive layer disposed along said second face of said gel;
    a voltage source in electrical communication with said first layer and said second layer;
    whereby upon application of a voltage potential across said layer of said gel by said voltage source, biomolecules in said gel are urged toward at least one of said first segment and said second segment of said traveling wave grid.

13. A process for separating various biomolecules from a sample, utilizing a gel electrophoretic system comprising (i) a layer of a gel suitable for electrophoresis, said gel layer disposed between two parallel substrates, (ii) a traveling wave grid, said grid including at least a first grid segment and a second grid segment, and (iii) a voltage controller in selective electrical communication with said first grid segment and said second grid segment, said voltage controller adapted to provide at least one multi-phase electrical signal, said process comprising:

depositing said sample on said layer of said gel;

applying a first multi-phase electrical signal from said voltage controller to at least one of said first grid segment and said second grid segment, to thereby cause at least a portion of biomolecules in said sample to migrate in said gel;

applying a second multi-phase electrical signal from said voltage controller to at least one of said first grid segment and said second grid segment to thereby cause (i) said portion of biomolecules to further migrate in said gel, or (ii) another portion of biomolecules in said sample to migrate in said gel.

14. The process of claim 13 wherein said step of applying said first multi-phase electrical signal is performed by applying said first signal to both said first grid segment and said second grid segment.

15. The process of claim 14 wherein said step of applying said second multi-phase electrical signal is performed by applying said second signal to said second grid segment.

16. The process of claim 13 wherein said system further comprises a voltage source in electrical communication with said layer of said gel, said process comprising:

applying a voltage potential across a thickness dimension of said layer of said gel.

17. The process of claim 13 wherein said system further comprises a second voltage controller in electrical communication with at least one of said first grid segment and said second grid segment, said second voltage controller adapted to provide at least one multi-phase electrical signal, said process comprising:

applying a third multi-phase electrical signal from said second voltage controller to at least one of said first grid segment and said second grid segment.

18. The process of claim 13 wherein said second multi-phase electrical signal is different than said first multi-phase electrical signal.

19. The process of claim 13 further comprising:

altering at least one of said voltage or frequency of one or more of (i) said first multi-phase electrical signal and (ii) said second multi-phase electrical signal.

20. The process of claim 13 wherein said first multi-phase electrical signal is a four (4) phase signal and said first grid segment includes a plurality of closely spaced parallel electrodes, said step of applying said first signal to said first grid segment includes (i) placing in electrical communication a first phase of said first signal with a first electrode of said plurality of electrodes, and placing in electrical communication said first phase of said first signal with a second electrode of said plurality of electrodes.

* * * * *